United States Patent [19]

Buysch et al.

[11] Patent Number: 5,087,754
[45] Date of Patent: Feb. 11, 1992

[54] PROCESS FOR THE PREPARATION OF N,N-DIALKYLANILINE

[75] Inventors: Hans-Josef Buysch, Krefeld; Heinrich Pelster, Odenthal-Gloebusch; Lothar Puppe, Burscheid; Peter Wimmer, Krefeld, all of Fed. Rep. of Germany

[73] Assignee: Bayer Aktiengesellschaft, Leverkusen, Fed. Rep. of Germany

[21] Appl. No.: 567,478

[22] Filed: Aug. 13, 1990

[30] Foreign Application Priority Data

Aug. 25, 1989 [DE] Fed. Rep. of Germany ....... 3928152

[51] Int. Cl.$^5$ ............................................. C07C 209/28
[52] U.S. Cl. .................................... 564/401; 564/395; 564/399; 564/409
[58] Field of Search ................ 564/401, 402, 409, 399

[56] References Cited

U.S. PATENT DOCUMENTS 4,801,752  1/1989  Chen et al. ........................ 564/401

FOREIGN PATENT DOCUMENTS 0327874  8/1989  Fed. Rep. of Germany .
327875  8/1989  Fed. Rep. of Germany .

OTHER PUBLICATIONS

Chemical Abstracts, vol. 108, No. 3, 1/18/88, p. 558 ref. no. 21483y Sato Haruhito et al: "Preparation of N-Alkylaniline Derivatives as Intermediates for drugs, agrochemicals, and color photography couplers."
Chemical Abstracts, vol. 84, No. 17, 4/26/76, p. 500 refn no. 121339K Takamiya Nobuo et al: "N-Methylation of Aniline with Methanol over Transition metal Zeolite."
Patent Abstracts of Japan vol. 12, No. 47 (C–475)(2894) 2/12/88 & JP A 62 195350 (Idemitsu Kosan) 8/28/87.

Primary Examiner—Glennon H. Hollrah
Assistant Examiner—Shailendra Kumar
Attorney, Agent, or Firm—Sprung Horn Kramer & Woods

[57] ABSTRACT

N,N-dialkylanilines can be prepared by reacting the anilines on which they are based with lower alcohols or with the corresponding ethers, at an increased temperature in the gas phase in the presence of a proton-containing zeolite catalyst of the pentasil type having an $SiO_2/Al_2O_3$ ratio of >60, it being advantageous to carry out the alkylation process under a pressure of 2–30 bar.

19 Claims, No Drawings

PROCESS FOR THE PREPARATION OF N,N-DIALKYLANILINE

BACKGROUND OF THE INVENTION

The invention relates to a process for the preparation of N,N-dialkylanilines by reacting anilines with lower alcohols or with the corresponding ethers at an increased temperature and increased pressure in the gas phase in the presence of proton-containing zeolites of the pentasil type.

It its known that N,N-dialkylated anilines can be prepared by reacting anilines with alcohols in the presence of acid catalysts, both in the liquid and in the gas phase. In the liquid-phase process, the reaction is carried out in the presence of a liquid catalyst, such as, for example, sulphuric acid, hydrochloric acid or phosphorus trichloride. These processes must be carried out under pressure. Because of the powerful corroding action of the acid catalysts, it is necessary to carry out the process in autoclaves which are especially resistant to corrosion. Yet, it is not possible to suppress corrosion completely. Moreover, there are substantial complications when the catalyst is removed and disposed of.

DE-AS (German Published Specification) 1,031,796 describes the reaction of aniline with alcohols in a way in which a mixture of aniline and excess alcohol is passed through hot, concentrated phosphoric acid. However, the selectivity for N,N-dialkyl compounds is low, in particular when it is intended to introduce alkyl radicals other than methyl. For example, in the case where ethyl is used as a radical, the temperature is 220° C. and the molar ratio of aniline/ethanol is 1:3, 51% of N-ethylaniline and 15% of N,N-diethylaniline are obtained. According to DE-OS (German Published Specification) 2,658,728, it is possible to improve the yield of N,N-diethylanilin when the process is carried out with the addition of aliphatic amines; conditions which are otherwise analogous give 44% of N-ethylaniline and 36% of N,N-diethylaniline. Apart from the corrosion problems which exist even here, such processes also have the disadvantage that the large amount of phosphoric acid becomes unusable as catalyst after some time and must be replaced by fresh phosphoric acid, with the result that waste disposal problems occur here, too.

U.S. Pat. No. 4,599,449 describes a process for gas-phase alkylation of aromatic amines with alcohols on transition metal oxide catalysts. However, the selectivity to N,N-dialkylanilines is very low. Even when a 5-fold excess of ethanol is used, the reaction rate of the aniline is not higher than 38% and thus very low, and N,N-diethylaniline is only obtained in unsatisfactory yields. Moreover, this process gives a high proportion of by-products which are alkylated on the ring.

DE-AS (German Published Specification) 2,335,906 teaches the N,N-dialkylation of arylamines with alcohols on silica catalysts which are covered with 0.1-20% by weight of phosphoric acid. To obtain good selectivities, however, a very large excess of alcohol of up to 20 mol equivalents is required. On the one hand, this results in a low space-time yield and, on the other hand, the separation and recyclization of the excess alcohol mean complicated distillation procedures. To avoid rapid deactivation of the catalyst and to ensure that its service life is long, it is additionally necessary continuously to add phosphoric acid and/or alkyl phosphates during the alkylation; however, a proportion of these phosphorus compounds is always discharged and contaminates the reaction product, thus requiring complicated separation procedures.

Furthermore, it is known that zeolites can be employed as catalysts for the gas-phase alkylation of aromatic amines with alcohols U.S. Pat. No. 4,801,752 suggest zeolites of the ZSM 5 type having a $SiO_2/Al_2O_3$ ratio of 20-700. However, flexible control of the yield in the direction of N,N-dialkylaniline is only possible to a limited extent, in particular when the radicals are other than the methyl radicals. The most favourable conditions give a maximum molar selectivity for N,N-diethylaniline of 10.1%. Moreover, temperatures up to above 400° C. must be used in this process. In addition, a significant proportion of unidentified by-products which are alkylated on the ring is obtained.

Japanese Patent 61/35,246 (1986) likewise describes zeolites having a medium pore size as catalysts for the gas-phase alkylation of aromatic amines with alcohols With these catalysts, it is possible to obtain N-monoalkylanilines in high selectivity, the text particularly stressing the fact that the formation of N,N-dialkylanilines on these catalysts is reduced. According to this publication, zeolites having a medium pore size are hence unsuitable for the dialkylation of aromatic amines.

There was therefore still a need to have available a catalytic process with which a large number of variously substituted anilines can be dialkylated on the N atom in the gas phase, this process not having the abovementioned disadvantages; in particular, desired alkyl radicals were those having more than one C atom. It was desired that the catalysts should be distinguished by uncomplicated availability, long service lives and high activities, and they should guarantee substantial reaction rates while having a good selectivity for N,N-dialkylation.

SUMMARY OF THE INVENTION

Surprisingly, it has now been found that these requirements are met when proton-containing zeolites of the pentasil type having a $SiO_2/Al_2O_3$ ratio of $>60$ are employed as catalysts and when the reaction is carried out under increased pressure. The process according to the invention guarantees the high yields and reaction rates which are required; alkylation on the ring only occurs to a low degree. The catalysts used have long service lives. The novel process was found to be dependent on the pressure, which is the more surprising since this contradicts Le Chatelier's Principle of Mobile Equilibrium. According to this law, such a dependence on pressure is not to be expected, since the reaction does not entail a contraction in volume.

The invention therefore relates to a process for the preparation of N,N-dialkylanilines by reacting the anilines on which they are based with lower alcohols or with the corresponding ethers at an increased temperature in the gas phase, which process is characterized in that the alkylation process is carried out in the presence of a proton-containing zeolite catalyst of the pentasil type having a $SiO_2/Al_2O_3$ ratio of $>60$ under a pressure of 2-30 bar.

DETAILED DESCRIPTION OF THE INVENTION

In a preferred manner, the process according to the invention is carried out under a pressure of 5-25 bar, and in a particularly preferred manner under a pressure of 8-20 bar.

The process according to the invention is carried out at a temperature of 200°–400° C., preferably 250°–350° C., and particularly preferably 260°–320° C. Before doing this, pressure and temperature are matched in such a way that all reactants are in the gas phase.

Zeolites which are suitable for the process according to the invention are pentasils which contain protons, that is to say, which are acid catalysts, and which have an $SiO_2/Al_2O_3$ ratio of $>60$. As cations, they can contain exclusively protons. However, up to 80% of the protons can be substituted by other cations. Cations suitable for this purpose are, for example, those of Na, K, Mg, Zn, Co, Cu, Ca, Fe, rare earths, such as, Ce, La and Ga, and Sn, Mn, Cr, Ti, Zr, and Ta. It is preferred to employ pentasils which have less than 80% metal cations, for example up to 50%, preferably up to 25%, particularly preferably up to 10%, and very particularly preferably up to 5%.

From the series of the pentasils, the following are preferably employed: ZSM 5, ZSM 11, ZSM 8, ZSM 5/ZSM 11 intermediates, Zeta 1, Zeta 3, ZMB 10, Ultrasil, Ultrazet, TZ-01, NU-4, NU-5, AZ-1. Such zeolites are known to the expert and have been described in many publications, for example in EP 54,386, EP 65,401, EP 34,727, EP 57,016 and EP 113,116 and also in Russ. J. Phys. Chem. 55 (1981), 1175. Zeolites which are particularly preferably employed are the following: ZSM 5, ZSM 8, ZSM 11 and ZSM 5/ZSM 11 intermediates; zeolites of the ZSM 5 type are very particularly preferably employed.

In the pentasil types to be employed according to the invention, the $SiO_2/Al_2O_3$ ratio should be wider than 60 and be, for example, 61–2,000, preferably 70–1,500, and particularly preferably 80–1,000. The preparation of the zeolites to be used is described in D. W. Breck: Zeolite Molecular Sieves, John Wiley and Sons Inc., New York 1974. In connection with the abovementioned zeolites of the pentasil type, mention may furthermore be made of U.S. Pat. No. 3,702,886, U.S. Pat. No. 3,709,979, GB 1,334,243 and EP 18,090.

To impart to the zeolites the form of pieces, which is more favourable for operating a gas-phase reactor, they are mixed with binders and the mixture is compressed and granulated. Suitable binders are various clays, alumosilicates and aluminum oxides, in particular $\gamma$-$Al_2O_3$, and silicon oxide. In the event that the gas-phase reaction is carried out in the fluidized bed, however, finely pulverulent zeolites are also suitable.

To carry out the process according to the invention, the aniline to be alkylated on the N atom and the alkylating agent (lower alcohol or corresponding ether) are evaporated, and the evaporated mixture is brought in contact with the zeolite catalyst. It is possible to add to the mixture used an inert gas as carrier gas, such as nitrogen, helium, steam, hydrogen or argon.

The load of the catalyst LHSV (Liquid Hourly Space Velocity) can be varied in the range of from 0.1–4.0 l/l/h, preferably from 0.3–2.0 l/l/h. In this context, LHSV is defined as the ratio of the volume of the liquid anilin/alcohol or aniline/dialkyl ether mixture per volume of catalyst per hour.

The reaction mixture is condensed at the reactor outlet and separated in a known manner, for example by distillation. Unreacted starting materials as well as N-monoalkylated products can be recycled to the reaction in a known manner.

In the process according to the invention, anilines of the formula (I) are reacted to give N,N-dialkylated anilines of the formula (II), in accordance with the equation below:

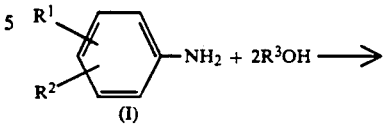

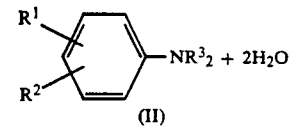

or

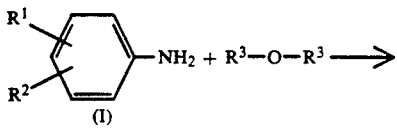

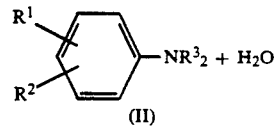

where
$R^1$ denotes hydrogen, straight-chain or branched $C_1$–$C_8$-alkyl, cyclohexyl, phenyl, straight-chain or branched $C_1$–$C_4$-alkoxy, fluorine, chlorine, bromine, cyano or nitro, $R^2$ represents hydrogen, straight-chain or branched $C_1$–$C_4$-alkyl, fluorine, chlorine or bromine, and $R^3$ denotes straight-chain or branched $C_1$–$C_4$-alkyl.

Straight-chain or branched $C_1$–$C_8$-alkyl is, for example, methyl, ethyl, propyl, isopropyl, butyl, isobutyl, tert.-butyl, the isomeric hexyls or octyls. The abovementioned $C_1$–$C_4$-alkyl radicals may be mentioned in a preferred manner. Methyl or ethyl may be mentioned in a particularly preferred manner.

Straight-chain or branched $C_1$–$C_4$-alkoxy is, for example, methoxy, ethoxy, propoxy, isopropoxy, butoxy or isobutoxy, preferably methoxy or ethoxy.

Preferred anilines to be reacted in the process according to the invention are those of the formula

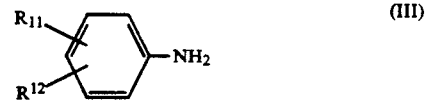

where
$R^{11}$ denotes hydrogen, methyl, ethyl, propyl, isopropyl, cyclohexyl, methoxy, ethoxy, fluorine or chlorine, particularly preferably hydrogen, methyl or chlorine, and very particularly preferably hydrogen or methyl, $R^{12}$ denotes hydrogen, methyl, ethyl, propyl, isopropyl, fluorine or chlorine, particularly preferably hydrogen, methyl or chlorine, and very particularly preferably hydrogen.

Anilines suitable for the process according to the invention are, for example, aniline, o-, m-, p-toluidine, o-, m-, p-chloroaniline, 2,4-, 2,6-, 3,4- or 3,5-xylidene, o-, m-, p-ethylaniline, o-, m-, p-isopropylaniline and others;

aniline and the abovementioned toluidines may be particularly emphasized.

The alcohols $R^3OH$ and their corresponding ethers $R^3$-O-$R^3$, mentioned in the above formulae for alkylation purposes, are known to the expert. The following may be mentioned as examples methanol, ethanol, propanol, isopropanol or the various butanols, or dimethyl ether, diethyl ether, dipropyl ether, diisopropyl ether or the various dibutyl ethers. In principle, mixed ethers are also to be reacted according to the invention, but these are less preferred because of the product mixtures obtained as a result.

The aniline to be alkylated and the alcohol or the ether are employed in a molar ratio of 1:2-10 (alcohol) or 1:1-5 (ether), respectively, preferably 1:3-5 or 1:1.5-2.5, respectively. When an ether is employed, the calculations are as for 2 moles of the corresponding alcohol.

N,N-dialkylanilines are important industrial intermediates for the preparation of dyes, plant protection agents and polymerization co-catalysts (Ullmanns Encyclopädie der technischen Chemie, [Ullmann's Encyclopedia of Industrial Chemistry/, 4th Edition, Vol. 7, p. 572-573; in English: 5th ed., Vol. A2, pp. 303).

EXAMPLE 1

A reaction tube in a vertical position, of length 50 cm and a diameter of 20 mm, was filled with 130 ml of a zeolite of the H-ZSM 5 type with an $SiO_2/Al_2O_3$ ratio of 320 and which had been bonded to 30% of a commercially available γ-aluminum oxide and which had a mean particle diameter of 1-2 mm. The reactor could be kept at constant temperature by means of a three-zone tube oven. The temperature in the packing of the catalyst could be measured by means of a mobile thermoelement and was 300° C. A pressure of 10 bar was maintained in the reactor via a pressure control valve. The loading of the catalyst (LHSV) was 1.0 1/1/h. The reaction product was condensed and analysed by gas chromatography. Reaction and selectivity are compiled in Table 1.

EXAMPLE 2

The procedure was as described in Example 1. The catalyst employed was a H-ZSM 5 zeolite having a $SiO_2/Al_2O_3$ ratio of 272.

EXAMPLE 3

The procedure was as described in Example 2. The mixture employed was an aniline/methanol mixture in the molar ratio of 1:2.

COMPARISON EXAMPLES 1 TO 3

The Comparison Examples were carried out under conditions analogous to the corresponding Examples, but at atmospheric pressure, that is to say at 1 bar.

The catalysts are distinguished by a long service life. After a service period of 300 h, conversion rate and yield were unchanged.

It is clear from Table 1 that operation at 10 bar results in a marked increase in conversion, combined with a comparably marked increase in the yield of N,N-dialkylated amine.

TABLE 1

| No. | $SiO_2/Al_2O_3$ | Alcohol | Aniline/alcohol (molar) | P (bar) | Conversion (mol %) | Ratio of di-/mono alkylaniline by weight |
|---|---|---|---|---|---|---|
| 1 | 326 | EtOH | 1:4 | 10 | 98 | 1.21 |
| Comp. Ex. 1 | 326 | EtOH | 1:4 | 1 | 79 | 0.44 |
| 2 | 272 | EtOH | 1:4 | 10 | 98 | 1.57 |
| Comp. Ex. 2 | 272 | EtOH | 1:4 | 1 | 89 | 0.69 |
| 3 | 272 | MeOH | 1:2 | 10 | 96 | 2.73 |
| Comp. Ex. 3 | 272 | MeOH | 1:2 | 1 | 91 | 1.79 |

N,N-dialkylation of aniline (Examples 1-3 and Comparison Examples 1-3) on H-ZSM 5 at 300° C.

What is claimed is:

1. A process for the preparation of an N,N-dialkylaniline by reacting the aniline on which it is based with a lower alcohol or with the corresponding ether at a temperature of 200°-400° C. in the gas phase, wherein the alkylation process is carried out in the presence of a proton-containing zeolite catalyst selected from the group consisting of ZSM 5, ZSM 11, ZSM 8, ZSM 5/ZSM 11 intermediates, Zeta 1, Zeta 3, ZBM 10, Ultrasil, Ultraset, TS-01, NU-4, NU-5, and AZ-1 having a $SiO_2/Al_2O_3$ ration of 60 under a pressure of 2-30 bar.

2. The process of claim 1, carried out under a pressure of 5-25 bar.

3. The process of claim 2, carried out under a pressure of 8-20 bar.

4. The process of claim 1, wherein the alkylation is carried out at 250°-350° C.

5. The process of claim 4, wherein the alkylation is carried out at 260°-320° C.

6. The process of claim 1, wherein 0-80 equivalent percent of the protons in the zeolite catalyst are substituted by metal cations selected from the group consisting of Na, K, Mg, Zn, Co, Cu, Ca, Fe, rare earths, such as, Ce, La and Ga, and Sn, Mn, Cr, Ti, Zr, and Ta.

7. The process of claim 6, wherein 0-50 equivalent percent of the protons in the zeolite catalyst are substituted by metal cations.

8. The process of claim 7, wherein 0-25 equivalent percent of the protons in the zeolite catalyst are substituted by metal cations.

9. The process of claim 8, wherein 0-10 equivalent percent of the protons in the zeolite catalyst are substituted by metal cations.

10. The process of claim 9, wherein 0-5 equivalent percent of the protons in the zeolite catalyst are substituted by metal cations.

11. The process of claim 1, wherien zeolite catalysts selected from the group consisting of ZSM 5, ZSM 8, ZSM 11 and ZSM 5/ZSM 11 intermediates are employed.

12. The process of claim 11, wherein a ZSM 5 zeolite catalyst is employed.

13. The process of claim 1, wherein the SiO$_2$/Al$_2$O$_3$ ratio is 61–2,000.

14. The process of claim 14, wherein the SiO$_2$/Al$_2$O$_3$ ratio is 70–1,500.

15. The process of claim 15, wherein the SiO$_2$/Al$_2$O$_3$ ratio is 80–1,000.

16. The process of claim 1, wherein the load of the catalyst LHSV is 0,1–4,0 1/1/h.

17. The process of claim 1, wherein an aniline of the formula

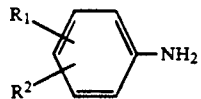

is reacted in which

R$^1$ denotes hydrogen, straight-chain or branched C$_1$–C$_8$-alkyl, cyclohexyl, phenyl, straight-chain or branched C$_1$–C$_4$-alkoxy, fluorine, chlorine, bromine, cyano or nitro, and R$^2$ represents hydrogen, straight-chain or branched C$_1$–C$_4$-alkyl, fluorine, chlorine or bromine.

18. The process of claim 1, wherein the alcohol or ether employed is one of the formulae R$^3$OH or R$^3$-O-R$^3$, respectively, in which R$^3$ denotes C$_1$–C$_4$-alkyl.

19. The process of claim 1, wherein the aniline to be alkylated and the alcohol or the ether are employed in a molar ratio of 1:2–10 (alcohol) or 1:1–5 (ether), respectively.

* * * * *

UNITED STATES PATENT AND TRADEMARK OFFICE
CERTIFICATE OF CORRECTION

PATENT NO. : 5,087,754

DATED : February 11, 1992

INVENTOR(S) : Buysch et al.

It is certified that error appears in the above-identified patent and that said Letters Patent is hereby corrected as shown below:

Col. 7, line 3   Delete " claim 14 " and substitute -- claim 13 --

Col. 7, line 5   Delete " claim 15 " and substitute -- claim 14 --

Signed and Sealed this

Thirteenth Day of July, 1993

Attest:

MICHAEL K. KIRK

Attesting Officer

Acting Commissioner of Patents and Trademarks